United States Patent
Brandt et al.

(10) Patent No.: US 11,141,551 B2
(45) Date of Patent: Oct. 12, 2021

(54) VENTILATION DRIVE FOR AN ANESTHESIA DEVICE AND METHOD FOR OPERATING SUCH A VENTILATION DRIVE

(71) Applicant: Drägerwerk AG & Co. KGaA, Lübeck (DE)

(72) Inventors: Andreas Brandt, Lübeck (DE); Ralf Heesch, Lübeck (DE); Marina Wahl, Schorndorf (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 926 days.

(21) Appl. No.: 15/749,625

(22) PCT Filed: Aug. 4, 2016

(86) PCT No.: PCT/EP2016/001343
§ 371 (c)(1),
(2) Date: Feb. 1, 2018

(87) PCT Pub. No.: WO2017/025178
PCT Pub. Date: Feb. 16, 2017

(65) Prior Publication Data
US 2018/0221606 A1    Aug. 9, 2018

(30) Foreign Application Priority Data
Aug. 7, 2015    (DE) .................... 10 2015 010 078.5

(51) Int. Cl.
*A61M 16/01*    (2006.01)
*A61M 16/08*    (2006.01)
*A61M 16/00*    (2006.01)

(52) U.S. Cl.
CPC .... *A61M 16/0069* (2014.02); *A61M 16/0057* (2013.01); *A61M 16/0063* (2014.02);
(Continued)

(58) Field of Classification Search
CPC ............ A61H 16/0069; A61H 16/0063; A61H 16/0081; A61H 16/0057; A61H 16/0066;
(Continued)

(56) References Cited

U.S. PATENT DOCUMENTS 5,678,540 A  *  10/1997  Kock ..................... A61M 16/00
                                                                  128/205.13
5,957,129 A  *  9/1999  Tham .................. A61M 16/104
                                                                  128/204.28
(Continued)

FOREIGN PATENT DOCUMENTS

DE    893 998 C      9/1954
DE    100 41 007 C1  9/2001
(Continued)

*Primary Examiner* — Timothy A Stanis
(74) *Attorney, Agent, or Firm* — McGlew and Tuttle, P.C.

(57) ABSTRACT

A ventilation drive (10) for an anesthesia device and a method for operating such a ventilation drive (10) are provided. The ventilation drive includes a blower unit (12), a pressure chamber (14) and a flexible bag (16) located in the pressure chamber (14). An internal volume of the bag (16) is coupled to an inspiratory branch (20) of a ventilation line. The blower unit (12) can be coupled to the internal volume of an outlet side and to an air inlet (26) for feeding ambient air on an inlet side. Further, a flow sensor (36) is provided between the outlet side of the blower unit (12) and the pressure chamber (14).

18 Claims, 5 Drawing Sheets

(52) U.S. Cl.
CPC .... *A61M 16/0066* (2013.01); *A61M 16/0081* (2014.02); *A61M 16/01* (2013.01); *A61M 2205/3334* (2013.01); *A61M 2205/3365* (2013.01)

(58) Field of Classification Search
CPC ............ A61H 16/01; A61H 2205/3334; A61H 2205/3365
See application file for complete search history.

(56) References Cited

U.S. PATENT DOCUMENTS

| | | | |
|---|---|---|---|
| 6,679,259 B2 | 1/2004 | Heesch | |
| 8,356,596 B2 | 1/2013 | Brandt et al. | |
| 2006/0283450 A1 | 12/2006 | Shissler et al. | |
| 2007/0163579 A1* | 7/2007 | Li | A61M 16/0081 128/203.14 |
| 2008/0196720 A1* | 8/2008 | Kollmeyer | A61M 16/024 128/204.21 |
| 2011/0214673 A1* | 9/2011 | Masionis | A61M 16/0078 128/205.13 |

FOREIGN PATENT DOCUMENTS

| | | |
|---|---|---|
| DE | 10 2004 011 907 A1 | 10/2005 |
| DE | 10 2008 057 180 B3 | 4/2010 |
| DE | 10 2010 035 167 A1 | 2/2012 |
| DE | 10 2013 011 983 A1 | 1/2015 |
| DE | 20 2014 000155 U1 | 3/2015 |
| EP | 2 168 623 A1 | 3/2010 |
| EP | 2 474 333 A1 | 7/2012 |
| WO | 2013/096495 A1 | 6/2013 |

* cited by examiner

Fig. 6

VENTILATION DRIVE FOR AN ANESTHESIA DEVICE AND METHOD FOR OPERATING SUCH A VENTILATION DRIVE

CROSS REFERENCE TO RELATED APPLICATIONS

This application is a United States National Phase Application of International Application PCT/EP2016/001343, filed Aug. 4, 2016 and claims the benefit of priority under 35 U.S.C. § 119 of German Application 10 2015 010 078.5, filed Aug. 7, 2015, the entire contents of which are incorporated herein by reference.

FIELD OF THE INVENTION

The present invention pertains to a ventilation drive for an anesthesia device as well as to a method for operating such a ventilation drive.

BACKGROUND OF THE INVENTION

A radial compressor acting as a ventilation drive and called a blower is known from DE 10 2013 011 983 A1. This is integrated into a ventilation line starting from a gas-mixing unit and ending in an inspiratory gas outlet. An inspiratory ventilation tube, which leads to the patient and by means of which a particular breathing gas being delivered by means of the ventilation drive enters the patient's lungs usually via the connection piece (Y-piece) as well as a downstream nasal mask or an endotracheal tube, can be connected to the inspiratory gas outlet (inspiratory port) of the anesthesia device.

A system with a driving gas source, by means of which a so-called bag-in-bottle system is driven via a double valve, is known from DE 10 2004 011 907 A1. A pressure sensor is provided in the vicinity of a Y-piece. A regulation is carried out in such a way that the double valve is actuated as a final control element, and the ventilation pressure of the pressure sensor at the Y-piece is used as the controlled variable.

A ventilation device with a turbine, whose speed can be regulated, is shown in DE 10 2010 035 167 A1. An ultrasound sensor, with which corresponding measured variables are detected, is provided in the vicinity of a Y-piece.

A piston system, as this is described in DE 100 41 007 C1, or a so-called bag-in-bottle system, may also be considered instead of a blower acting as a ventilation drive. The ventilation is carried out in the case of a bag-in-bottle system by means of a flexible bag, which is located in a rigid housing acting as a pressure chamber (bottle). The gas volume present in the bag is displaced to the patient when pressure is applied to the pressure chamber. The patient is ventilated in this manner. When the patient is exhaling, breathing gas flows back into the bag. The application of pressure to the pressure chamber accommodating the bag is controlled for a displacement of breathing gas volume from the bag to the patient and from the patient back into the bag, which displacement is sufficient for a preset or presettable ventilation profile, and pressure and/or flow measured values are recorded and monitored for this on the patient side.

Such a bag-in-bottle system is characterized by a simple configuration and good visibility of the ventilation based on the moving bag. In addition, a bag-in-bottle system can be cleaned easily and the bag or the bag and the pressure chamber can be disposed of in a simple and comparatively uncomplicated manner.

SUMMARY OF THE INVENTION

One object of the present invention is correspondingly to provide an additional embodiment of a ventilation drive with the advantages of a bag-in-bottle system as well as a method for operating such a ventilation drive.

This object is accomplished according to the present invention. The following provisions are made for this in a ventilation drive, especially in a ventilation drive intended for use in an anesthesia device: The ventilation drive comprises—as a bag-in-bottle system—a pressure chamber and a flexible bag located in the pressure chamber. The bag is connected within the pressure chamber acting as a pressure-stable housing at least to an inspiratory branch of a ventilation line. The previous port for introducing driving gas into the pressure chamber is replaced by a blower unit, which is sometimes also called blower module, with an impeller, which is driven especially by an electric motor. The blower module can be coupled on its outlet side to the pressure chamber, namely, to the inner volume of the pressure chamber, which volume remains outside the bag, and is coupled to the pressure chamber in this manner at least at times.

A flow sensor is provided between the outlet side of the blower unit and the pressure chamber or the inner volume of the pressure chamber. This flow sensor is configured for providing a flow sensor signal. A flow sensor may also be called a volume flow sensor in the sense of this application. The flow sensor is preferably configured as a bidirectional flow sensor. The flow sensor is preferably a so-called delta-P sensor.

A control unit, which is configured to detect the flow sensor signal as a measured variable and to change a speed of the blower unit as a function of the flow signal of the flow sensor, is preferably provided.

An inlet side of the blower module makes it possible to feed ambient air into the blower module. The blower module can be coupled for this to an air inlet on its inlet side and is coupled to this at least at times. Ambient air is accordingly drawn from the surrounding air by means of the ventilation drive during the operation of the blower module at least during a certain phase of the operation by means of the impeller now rotating and is delivered into the inner volume of the pressure chamber that is located outside the bag. This inner volume is defined by the pressure-stable housing of the pressure chamber, on the one hand, and the outer side of the bag, on the other hand. As soon as a pressure thus generated in the pressure chamber or in the inner volume exceeds a pressure in the bag or in an inner area of the bag, the bag is compressed and part of the gas volume (breathing gas) present in the bag is gradually displaced into the inspiratory branch connected to the bag and from there to the particular patient.

The above-mentioned object is accomplished in terms of the method with the features of the second independent claim. Provisions are made here for the operation of the ventilation drive of the type here and hereinafter described for ambient air to be drawn in from the surrounding area by means of the blower unit and to be delivered into the pressure chamber, namely, to compress the bag as well as to displace a part of a breathing gas volume present in the bag into the inspiratory branch. The ambient air being delivered by means of the blower unit into the pressure chamber now enters the inner volume of the pressure chamber that remains outside the bag, so that the pressure in the interior of the pressure chamber and outside the bag increases with increasing flow rate produced by the blower unit and the bag is thus compressed and, as a consequence, a part of the breathing gas volume present in the bag is displaced into the inspiratory branch.

One of the advantages of the ventilation drive being proposed here is that by means of the blower unit (blower module) and by means of the ambient air delivered by it into the pressure chamber, it is possible to compress the bag in the pressure chamber just as it was done hitherto by means of a special driving gas. An overpressure in the pressure chamber necessary for displacing breathing gas volume from the bag to the patient and hence the pressure acting on the flexible bag were hitherto generated by means of a driving gas, which is usually available in a medical setting. This driving gas was displaced from the pressure chamber during the exhalation by the patient and released into the surrounding area, so that this resulted in the consumption of a large quantity of driving gas. The driving gas is, for example, medical compressed air or medical oxygen, which air or oxygen is available in a medical grade in a patient room or in an operating room in a manner known per se, for example, via an outlet of a central gas supply system. At any rate, the particular gas is not made available exclusively as driving gas and is consumed in case of use as a driving gas, so that corresponding costs will result. However, the gas delivered into the pressure chamber by means of the blower unit according to the solution being proposed here is ambient air, which is available more or less at no cost or at a low cost, so that the subsequent release of this gas into the surrounding area during the expiratory phase is also unproblematic. The ventilation drive is thus independent in this manner from the availability of special driving gases. The blower unit is operated electrically. The electrical energy necessary for this may originate from a central network or also from a medical device, which comprises such a ventilation drive, i.e., for example, an anesthesia device, battery cells as standard accessory or the like.

In summary, a key advantage of the innovation being proposed here is that the ventilation drive does not consume any medical gases for driving purposes and also has, at least essentially, the advantages of the bag-in-bottle system outlined above in terms of good observability of the ventilation process and easy cleaning.

It can further be stated in summary that an essential advantage is that generally advantageous properties of a blower module, such as unrestricted spontaneous breathing, the enabling of a gentle ventilation, low internal resistance coupled with the hygienic advantages of a bag-in-bottle system, are achieved. Further, need for an otherwise necessary compressed air source for the ventilation drive is eliminated.

A general advantage of the ventilation drive being proposed here is that neither the blower unit nor the sensor system of the ventilation drive are located in the breathing circuit and contamination as well as an impairment of function due to the dust of the breathing line are correspondingly ruled out as well. Finally, the bag may also be configured as a "disposable" bag due to the bag membrane consisting, for example, of a favorable elastomer and being able to be discarded and disposed of after use. This is advantageous in case of highly infectious patients. The complete part contaminated with anesthetic gas, i.e., at least the bag, can also be removed and replaced in case of so-called malignant hyperthermia.

It is also possible to control and change the speed of the blower unit by means of a flow measurement uncoupled from the breathing gas by means of a sensor system comprising at least one flow sensor. A volume flow-controlled ventilation or a volume-controlled ventilation preferably takes place here. The flow measurement is highly accurate now also because only the flow of the ambient air flowing in the direction of the pressure chamber or the flow of the air leaving the pressure chamber is detected. Distortions due to different gases, as this may happen in case of different anesthetic gases, or distortions based on moisture or different moisture conditions during inhalation and exhalation are not to be expected here. Another advantage is that unlike in other systems, the flow sensor is not located in the breathing circuit in the solution being proposed here and therefore it also does not have to be sterilized. This offers the possibility of reducing costs. In addition, the flow sensor does not come into contact with anesthetic gases, so that the duration during which the flow sensor can be used increases markedly.

The control unit is preferably configured to change the speed of the blower unit as a function of the flow sensor signal as well as of a preset flow set point.

The control unit is preferably configured to change the speed of the blower unit here as a function of the flow sensor signal as well as of the preset flow set point such that a volume flow-controlled ventilation is carried out.

The control unit is preferably configured to change the speed of the blower unit as a function of the flow sensor signal as well as of a preset tidal volume set point.

The control unit is preferably configured to determine a tidal volume from the flow sensor signal as well as further to change the speed of the blower unit as a function of the determined tidal volume and of the preset tidal volume set point, especially such that a volume-controlled ventilation is carried out.

A pressure sensor is preferably provided, wherein a control unit is provided and configured to change a speed of the blower unit as a function of a pressure sensor signal of the pressure signal. The pressure is preferably provided between the outlet side of the blower unit and the pressure chamber or the inner volume of the pressure chamber. As an alternative, the pressure sensor is provided in the breathing circuit, especially at an inspiratory port or an expiratory port. A ventilation tube is connected at such a port to the anesthesia device, the ventilation tube leading to a patient, preferably via a Y-piece.

The control unit is preferably configured to change the speed of the blower unit as a function of the pressure sensor signal as well as of a preset flow set point such that a pressure-controlled ventilation is carried out.

It shall be noted that the ventilation drive may also be perfected according to the features of the method described below, such that the ventilation drive comprises means for configuring the respective embodiment of the method and of the method steps comprised thereby. The method for operating the ventilation drive may likewise be perfected corresponding to the functionality of the material aspects of the ventilation drive.

The above-described possibility of coupling the blower unit to the pressure chamber on the outlet side and to the air inlet for feeding ambient air on the inlet side is ensured at any time. However, this coupling is ensured during the operation of the ventilation drive during a special phase of the operation only, namely, during a phase of operation during which gas shall be displaced by means of the ventilation drive from the bag located in the pressure chamber in the direction of the patient (inspiratory phase). The blower unit can be deactivated and the pressure chamber can be opened for pressure equalization during a subsequent expiratory phased, i.e., when breathing gas flows back into the bag. A connection line between the outlet side of the blower unit and the pressure chamber may likewise be opened by means of a valve or the like. The opening of the pressure chamber or of the connection line causes, even if the blower unit is still in operation and there is a corresponding volume flow originating from the blower unit, this volume flow to escape through the opening and to at least fail to contribute to a pressure increase in the pressure chamber, and a pressure equalization, which is necessary when breathing gas flows back into the bag, to likewise take place in the pressure chamber via the opening.

A directional control valve is located in one embodiment of the ventilation drive between the blower unit and the pressure chamber, and a first gas path can be switched by means of the directional control valve for ambient air drawn in by means of the blower unit into the pressure chamber and a second gas path can be switched for air leaving the pressure chamber, especially for air drawn off from the pressure chamber by means of the blower unit. The advantage of the use of a directional control valve as a switching element is that it is possible to switch back and forth between the above-mentioned first gas path and the second gas path by means of one and the same switching element. During the operation of the ventilation drive, the ventilation drive is switched over cyclically between an inspiratory phase and an expiratory phase, and the switchover comprises a switching over of the directional control valve, such that the first gas path for ambient air drawn in by means of the blower unit is switched (released) into the pressure chamber during the inspiratory phase by means of the directional control valve and that the second gas path for air leaving the pressure chamber is switched (released) during the expiratory phase.

In another embodiment of the ventilation drive, the ventilation drive comprises a gas path from the directional control valve to an inlet side of the blower unit, which gas path is called bypass here for distinction. In the switched position of the directional control valve that connects the pressure chamber to the bypass, the pressure chamber is finally connected to the inlet side of the blower unit, so that air can be drawn off from the pressure chamber by means of the blower unit. A switchover of the flow direction of the air moving within the ventilation drive is thus achieved by means of the directional control valve: An outlet side of the blower unit is connected to the pressure chamber by means of the directional control valve in a first switching position of the directional control valve. Ambient air is delivered into the pressure chamber via this gas path during the operation of the blower unit, and a resulting displacement of breathing gas from the bag located in the interior of the pressure chamber leads to ventilation of the patient (inspiratory phase). In a second switching position of the directional control valve, an inlet side of the blower unit is connected to the pressure chamber by means of the directional control valve. Ambient air delivered before into the pressure chamber is again drawn off from the pressure chamber (expiratory phase) via this gas path during the operation of the blower unit. The patient's work of breathing is supported in this manner and breathing gas exhaled from the lungs flow back into the ventilation line and into the bag located in the pressure chamber. It is likewise possible to optimize the fresh gas consumption, for example, on the basis of the method described in DE 100 41 007 C1 (corresponding to U.S. Pat. No. 6,679,259). Switching over is performed continuously back and forth between the first switching position of the directional control valve and the resulting inspiratory phase as well as the second switching position of the directional control valve and the resulting expiratory phase during the operation of the ventilation drive during the ventilation of a patient.

In yet another embodiment of the ventilation drive, the ventilation drive comprises a pressure sensor and/or a flow sensor—hereinafter called individually and jointly sensor system—behind an outlet side of the blower unit and between the blower unit and the pressure chamber. The ventilation of a patient by means of the ventilation drive can be accurately monitored by means of such a sensor system and of a measured value that can be obtained therefrom, so that in case of an error, for example, in case of an excessively high or excessively low pressure measured value, it is possible to send an alarm message, which alerts the operating staff to the existing exceptional situation. Moreover, at least one such measured value is also the basis for a control or regulation of the ventilation drive.

The ventilation drive being proposed here is a pressure source and hence it is ideal for a pressure-controlled ventilation of the patient in question. Such a pressure-controlled ventilation is possible using a measured value of a sensor system comprising at least one pressure sensor. The pressure sensor is preferably located entirely outside the breathing circuit and comes only into contact with the air flowing to the pressure chamber or escaping from the pressure chamber, so that a special contamination is not to be expected and, at any rate, no sterilization of the pressure sensor is necessary.

An exemplary embodiment of the present invention will be explained in more detail below on the basis of the drawings. Objects or elements corresponding to one another are designated by the same reference numbers in all figures.

The exemplary embodiment or each exemplary embodiment shall not be considered to represent a limitation of the present invention. Variations and modifications, especially such variants and combinations that the person skilled in the art can find in respect to accomplishing the object, for example, through combination or variation of individual features described in connection with the general or special part of the description as well as contained in the claims and/or in the drawings and lead to a new object through features that can be combined, are rather possible within the framework of the present disclosure. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
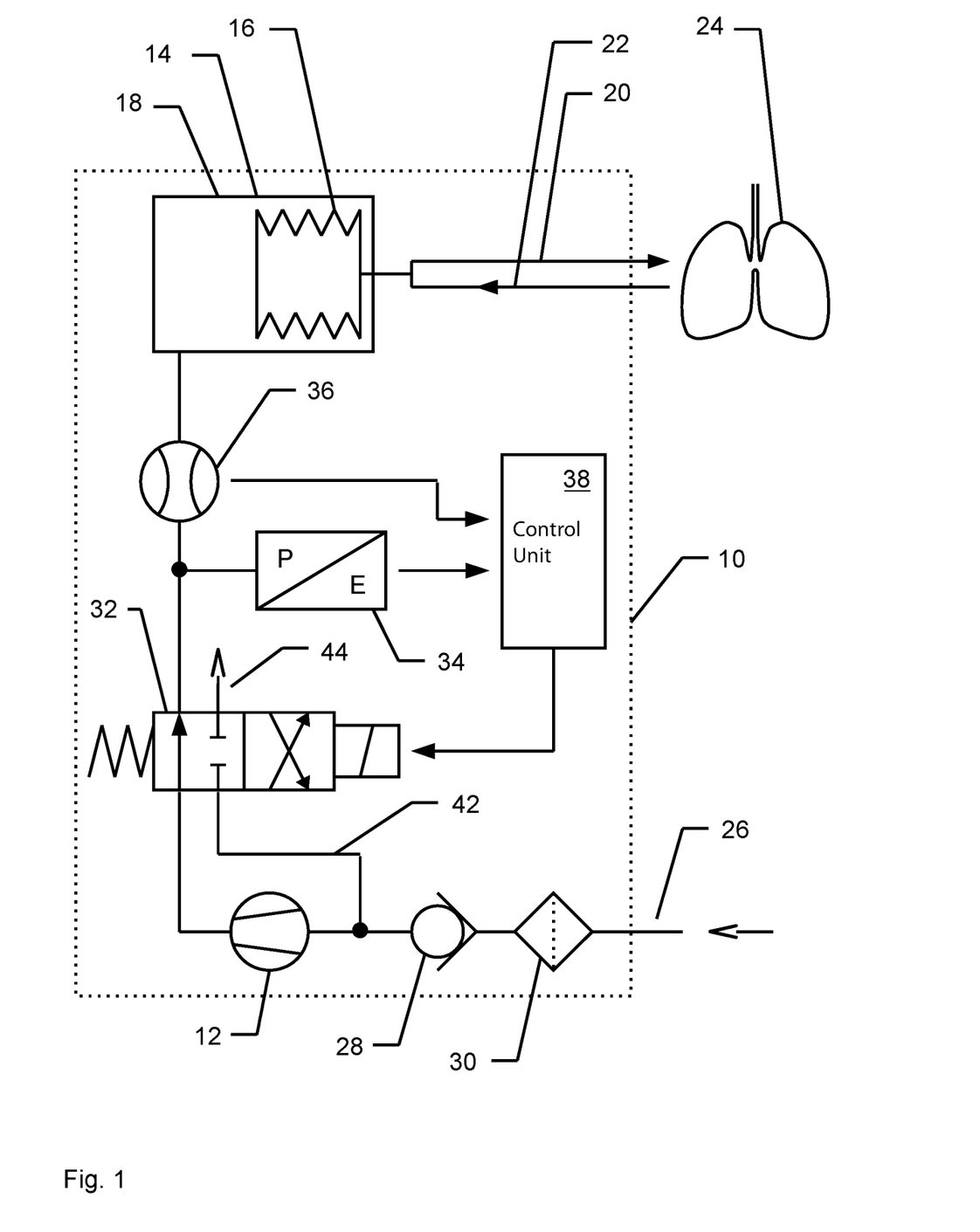
FIG. 1 is a schematic view showing a ventilation drive.

Referring to the drawings, the view in FIG. 1 shows an embodiment of a ventilation drive 10 corresponding to the solution being proposed here in a schematically highly simplified manner. The ventilation drive 10 comprises a blower unit 12, which is sometimes also called blower module or blower for short, a pressure chamber 14 and a flexible bag 16 located in the pressure chamber 14. The pressure chamber 14 and the bag 16 together form a so-called bag-in-bottle unit (bag-in-bottle system) 18, which is known per se, in principle. The interior space of the bag 16 is coupled at least to an inspiratory branch 20 of a ventilation line, usually, as is also shown in the view in FIG. 1, to an inspiratory branch 20 and to an expiratory branch 22 of the ventilation line, but details of a breathing circuit, which is known per se, in principle and comprises the inspiratory branch as well as the expiratory branch 20, 22, respectively, are not shown here. It is nevertheless suggested that breathing gas displaced from the bag 16 by means of the inspiratory branch 20 is moved in the direction of a patient to be ventilated, namely, the lungs 24 of said patient, and that gas exhaled by means of the expiratory branch 22 is moved at least again into the breathing circuit and in the direction of the bag 16. This movement of gas (breathing gas, patient gas) is brought about by means of the ventilation drive 10 and the blower unit 12 comprised by same. This unit is coupled to the internal volume of the pressure chamber 14 surrounding the bag at least indirectly on the outlet side and permits the feed of ambient air on an inlet side. Ambient air is drawn in at an air inlet 26 by means of the blower unit 12 at least during a certain phase of operation of the ventilation drive 10 during the operation of ventilation drive 10 and of a correspondingly activated blower unit 12 and is delivered into the pressure chamber 14. As soon as an overpressure develops in this manner in the pressure chamber 14 relative to the pressure in the bag 16, the bag is compressed and a part of the breathing gas volume present in the bag 16 is displaced into the inspiratory branch 20.

A nonreturn valve 28 and a filter element 30 are located upstream of the blower unit 12 on an inlet side of the ventilation drive 10. Downstream of the blower unit 12, the ventilation drive 10 comprises a directional control valve 32 acting as a switching element as well as a pressure sensor 34 and/or a flow sensor 36.

The pressure sensor 34 is preferably provided between the outlet side of the blower unit and the pressure chamber or the internal volume of the pressure chamber. As an alternative, the pressure sensor is provided in the breathing circuit, especially at an inspiratory port or at an expiratory port. A ventilation tube is connected to the anesthesia device at such ports, and the ventilation tube leads to a patient, preferably via a Y-piece.

The directional control valve 32 can be actuated electromagnetically and is optionally reset by spring action. A control unit 38 is provided for actuating the directional control valve 32. The control unit 38 comprises, in a manner known, in principle, per se, a processing unit in the form of or in the manner of a microprocessor as well as a memory, into which a control program is loaded, which is executed during the operation of the ventilation drive 10 by means of the processing unit of the control unit 38 and determines the functionality of the control unit 38 and hence also the functionality of the ventilation drive 10 as a whole.

A flow sensor 36 is consequently provided for providing a flow sensor signal between the outlet side of the blower unit 12 and the pressure chamber 14 or the internal volume of the pressure chamber 14. The flow sensor 36 preferably has a bidirectional configuration. The flow sensor 36 is preferably a so-called delta-P sensor.

A pressure sensor 34 is consequently provided for providing a pressure sensor signal between the outlet side of the blower unit 12 and the pressure chamber 14 or the internal volume of the pressure chamber 14. As an alternative, the pressure sensor is provided in the breathing circuit, especially at an inspiratory port or at an expiratory port. A ventilation tube is connected to the anesthesia device at such ports, the ventilation tube leading to a patient, preferably via a Y-piece.

A ventilation profile 40 (FIG. 4) can, in principle, be preset for the control unit 38 in a manner known per se. For example, a pressure curve is obtained during an inspiratory phase and a pressure curve is obtained during an expiratory phase based on the ventilation profile 40 as well. To guarantee the actual pressure conditions in the ventilation line, measured values from the pressure sensor 34 (pressure measured value, illustrated by the arrow from the pressure sensor 34 to the control unit 38) are recorded and monitored by means of the control unit 38. Measured values from the flow sensor 36 (flow measured value illustrated by the arrow from the flow sensor 36 to the control unit 38) are recorded and monitored by means of the control unit 38 in case of volume-controlled ventilation as opposed to such a pressure-controlled ventilation.

The control unit 38 is consequently configured, in principle, to detect a pressure sensor signal of the pressure sensor 34 as a measured variable and to change or control a speed of the blower unit as a function of the measured variable or of the pressure sensor signal. This will still be explained in detail later.

The control unit 38 is likewise configured, in principle, to detect the flow sensor signal of the flow sensor 36 as a measured variable and to change or control a speed of the blower unit as a function of the measured variable or of the flow sensor signal. This will still be explained in detail later.

In the interest of better comprehensibility of the following description, the pressure sensor 34 and the flow sensor 36 will hereinafter be called, individually or together, a sensor system 34, 36 as well as the pressure and/or flow measured value or each pressure and/or flow measured value originating from the sensor system 34, 36, also called pressure sensor signal or flow sensor signal, will also be called measured value. The blower unit 12 is actuated by means of the control unit 38 corresponding to the respective ventilation profile 40 and the measured value that can be obtained in respect to the ventilation drive 10 by means of the sensor system 34, 36.

Further, the directional control valve 32 (control signal(s) for actuating the directional control valve 32; illustrated by the arrow from the control unit 38 to the directional control valve 32) is preferably actuated by means of the control unit 38.

The directional control valve 32 is switched during the inspiratory phase such that ambient air drawn in by means of the blower unit 12 enters the pressure chamber 14 of the bag-in-bottle unit 18 (switching position according to the view shown in FIG. 1). The flow of gas between the blower unit 12 and the pressure chamber 14 is switched over during the subsequent expiratory phase (the corresponding switching position of the directional control valve 32 is shown in the view in FIG. 2). The pressure chamber 14 is coupled now to the inlet side of the blower unit 12 by means of a bypass 42 and a corresponding switching position of the directional control valve 32. Based on this switchover, the blower 12 draws off the gas located in the pressure chamber 14 or the air (previous ambient air). Based on the pneumatic resistance, which is formed by the nonreturn valve 28, a vacuum, namely, a vacuum sufficient for drawing off the gas located in the pressure chamber 14, is formed between the nonreturn valve 28 and the blower unit 12. The nonreturn valve 28 generates a constant vacuum or a vacuum dependent on the particular air flow or a vacuum in the form of a combination of the two. The air drawn off is released via the directional control valve 32 and an outlet 44 following the directional control valve 32 into the surrounding area. The ambient air drawn in during the inspiratory phase and delivered into pressure chamber 14 by means of the blower unit 12 as well as the air drawn off from the pressure chamber 14 by means of the blower unit 12 during the expiratory phase is separated now by the bag 16 at any time from the breathing gas located in the bag 16 and in the ventilation line.

The possibility of drawing off the gas located in the pressure chamber 14 by means of the ventilation drive 10 also makes an emergency ventilation. A shut-off valve 45, which can be actuated and is closed in the normal case, is shown for this in the FIG. 3, which is a repetition of the view according to FIG. 2, in the ventilation line comprising the inspiratory branch 20 and the expiratory branch 22 or in the breathing circuit adjoining it. A possibility of switching over between the inspiratory branch 20 during the inspiratory phase and the expiratory branch 22 during the expiratory phase by means of one valve or a plurality of valves is not shown.

The shut-off valve 45 is opened automatically following the exhalation by the patient in case of a failure of the fresh gas supply in the breathing circuit and an emergency ventilation, which is now necessary. The expiratory phase is prolonged for this and an actuation, which brings about an opening of the shut-off valve 45, can take place, for example, by means of a corresponding control signal of the control unit 38 of the ventilation drive 10, for example, under the condition that an emergency ventilation is necessary, that the ventilation drive 10 is in the phase of operation "exhalation" and that a volume flow in the expiratory branch 22 reaches or drops below a preset threshold value, for example, a threshold value equal to zero or close to zero, the latter for determining the end of the exhalation process of the patient. The shut-off valve 45 can thus definitely also be considered to be part of the ventilation drive 10. The shut-off valve 45 is at least a part of an anesthesia device, which comprises the ventilation drive 10 and is not shown itself. Due to the shut-off valve 45 being opened in case of an emergency ventilation subsequent to the exhalation process of the patient, air is drawn into the breathing circuit via the shut-off valve 45 during the further drawing off of the gas located in the pressure chamber 14 by means of the ventilation drive 10 during the prolonged expiratory phase. The ambient air drawn in previously is delivered to the patient during the subsequent inspiratory phase during the compression of the bag 16 by means of the ventilation drive 10. The shut-off valve 45 is optionally closed automatically, for example, by means of a corresponding control signal of the control unit 38, the inspiratory phase. The automatic actuation for opening the shut-off valve 45 during the expiratory phase and subsequent to the exhalation process of the patient takes place as long as emergency ventilation is necessary. If no emergency ventilation is necessary, the shut-off valve 45 is closed. Whether a situation that requires an emergency ventilation is present is signaled to the control unit 38, for example, by means of an external control signal (in the form of the arrow shown on the right-hand side of the control unit 38 in the view shown in FIG. 3). The control signal may originate from an anesthesia device comprising the ventilation drive 10, for example, from the control unit thereof. As an alternative, the control signal may also originate from a pressure sensor or a gas sensor in the ventilation line.

Figure 4:
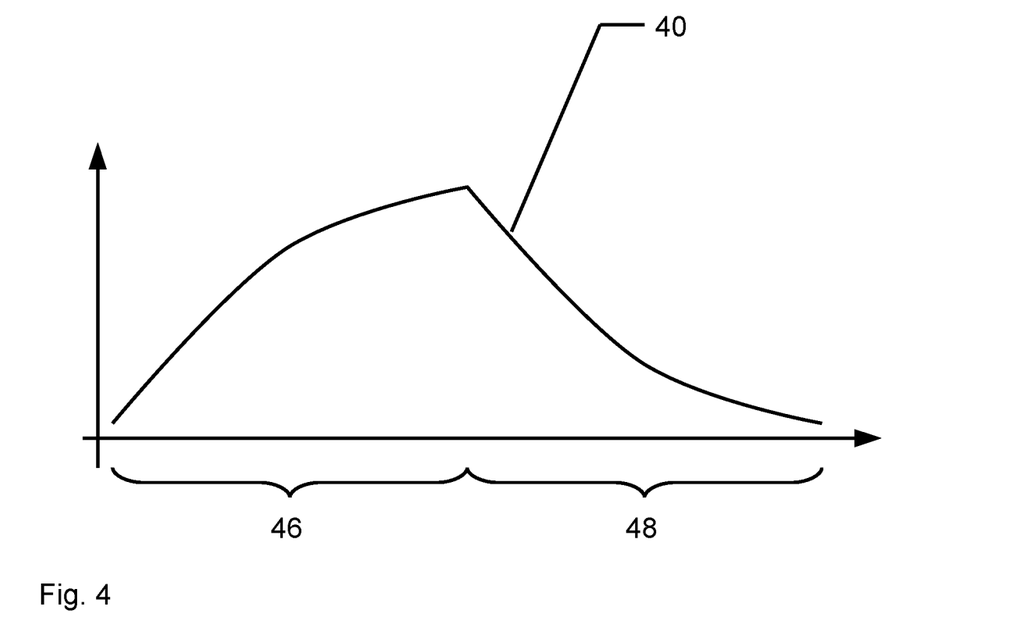
FIG. 4 is a graph showing a ventilation profile.
Figure 5:
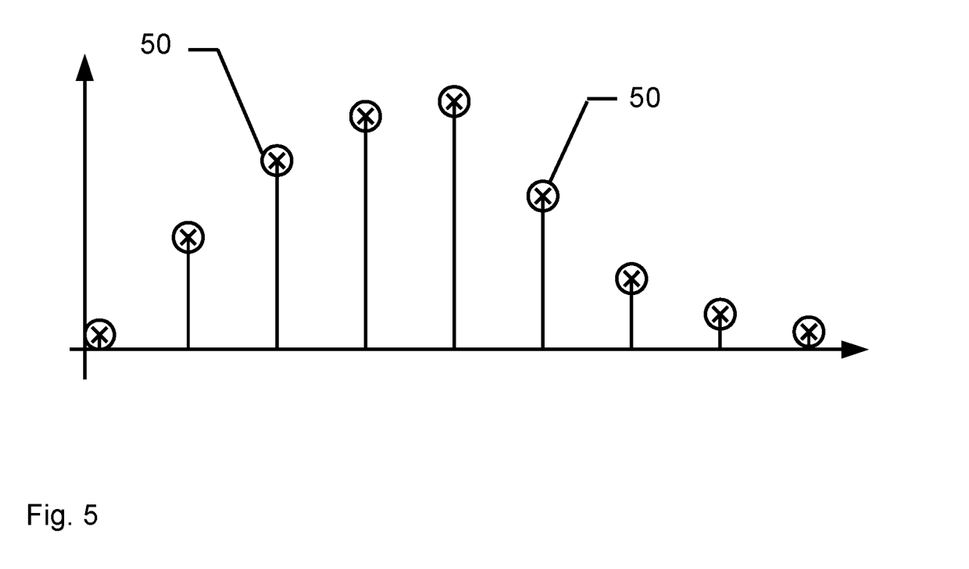
FIG. 5 is a graph showing support points of the ventilation profile according to FIG. 4.

A ventilation profile 40 with an inspiratory phase 46 and with an expiratory phase 48 are shown in the view in FIG. 4 in a schematically simplified manner. The respective ventilation profile 40 is obtained, in a manner known per se, in principle, based on corresponding specifications of an operator on the control unit 38 or on a higher-level control unit (not shown), for example, a control unit of an anesthesia device, likewise not shown, which comprises a ventilation drive 10 of the type shown here. Characteristic values of the ventilation profile 40 are transferred to the control unit 38 in the latter case by means of the higher-level control unit subsequent to the specification of a ventilation profile 40 there. At any rate, after presetting the ventilation profile 40, the control unit 38 of the ventilation drive 10 has characteristic values, which describe the particular ventilation profile 40, for example, values in the form of support points 50 of the ventilation profile 40, as this is shown in the view shown in FIG. 5. These characteristic values may also be modified by the control unit, for example, by way of adaptation to particular local ambient pressure and/or for adaptation to a pressure changed by the elasticity of the bag 16 and/or the weight of the bag 16.

The particular local ambient pressure can be determined by means of an absolute pressure sensor, not shown here, or on the basis of an input possibility for presetting the geodetic height at which the anesthesia device comprising the ventilation drive 10 is operated. In a special embodiment, the determination of the local ambient pressure and the correction of the ambient pressure are carried out without an additional ambient pressure sensor. A calibration is performed for this in relation to the ambient pressure during the switchover between the inspiratory phase and the expiratory phase, i.e., when breathing gas is not delivered either via the inspiratory branch 20 to the lungs 24 or via the expiratory branch 22 back into the breathing circuit and in the direction of the bag 16 (dispensed flow=0). This calibration is based on a measurement of the instantaneous pressure at the time of switchover (dispensed flow=0) by means of the pressure sensor 34. At the same time, a speed of the blower unit 12, namely, a speed of a fan impeller of the blower unit 12, is determined. Based on a characteristic, which is specific of the particular blower unit 12 and whose data are stored, for example, in the control unit 38, the ambient pressure can be determined with the measured pressure and the speed in a manner that is known per se.

Such support points 50 shall expressly be considered to be an example only. It can equally be considered that the control unit 38 has a mathematical description of the ventilation profile 40 or individual segments of the profile 40 as characteristic values of the ventilation profile 40. Without abandoning a further general validity, the following explanations will be continued here on the basis of a description of the ventilation profile 40, which is available to the control unit 38 in the form of support points 50. The control unit 38 can now determine a particular value that is necessary according to the ventilation profile 40, for example, a pressure set point, at any time (intermediate values are determined by interpolation) and compare it with a measured value determined by the sensor system 34, 36, for example, with a pressure measured value available from the pressure sensor 34. The speed of the blower unit 12, namely, the speed of a fan impeller of the blower unit 12, is adapted on the basis of a deviation between a particular pressure set point as well as a particular pressure measured value by means of a control algorithm, which is comprised by the control unit 38 and is accordingly implemented in software.

It can be stated, in summary, that the control unit 38 performs the adaptation or control of the speed of the blower unit 12 as a function of the pressure measured value or pressure sensor signal of the pressure sensor 34 and of a preset pressure set point. The control unit 38 derives for this a pressure measured value from the pressure sensor signal and determines a difference between the pressure measured value and a preset pressure set point. This pressure difference is then converted by the control unit 38 into a speed set point of the blower unit 12, preferably by means of a data set, which has a characteristic. Such a characteristic relates pressure values to speeds of the blower unit. The control unit selects a control signal for the blower unit 12 such that the blower unit 12 assumes or implements the speed set point. The control unit 38 consequently changes or controls the speed of the blower unit 12 as a function of the pressure sensor signal as well as a preset pressure set point such that a pressure-controlled ventilation is carried out.

The speed of the blower unit 12 can also be changed or controlled by means of the control unit 38 on the basis of the flow measured value or the flow sensor signal of the flow sensor 36 as a function of the flow sensor signal of the flow sensor.

The control unit 38 preferably carries out a change or control of the speed of the blower unit 12 as a function of the flow sensor signal as well as of a preset flow set point. The control unit preferably carries out a change or control of the speed of the blower unit 12 as a function of the flow sensor signal as well as of a preset flow set point such that a volume flow-controlled ventilation is carried out. The control unit 38 derives for this a flow value or volume flow value from the flow sensor signal and compares this with the preset flow set point or the preset volume flow value. The control unit 38 derives a pressure set point, which shall be generated by the blower unit 12, from a difference of the derived flow value and the preset flow set point. The control unit 38 then derives from this pressure set point a speed set point, preferably by means of a data set, which has a characteristic. Such a characteristic relates pressure values to speeds of the blower unit. The control unit 38 then selects a control signal for the blower unit 12 such that the blower unit 12 assumes or implements the speed set point.

In other words, the control unit 38 is configured to determine a particular value that is necessary according to the ventilation profile 40, e.g., a volume flow set point, at different times, preferably by intermediate values by means of interpolation. The control unit 38 can compare this volume flow value with a measured value obtained from the sensor system 34, 36, for example, with a volume flow measured value that can be obtained from the volume flow sensor 36. The speed of the blower unit 12, namely, the speed of a fan impeller of the blower unit, is adapted by means of a control algorithm comprised by the control unit 38 and accordingly implemented in software on the basis of a deviation between a respective volume flow set point as well as a particular volume flow measured value.

The control unit is preferably configured to change or control the speed of the blower unit as a function of the flow sensor signal as well as of a preset tidal volume set point. The control unit now detects the flow sensor signal of the flow sensor 36 and determines a tidal volume from this. This is preferably carried out by the flow sensor signal or the corresponding flow measured value being integrated over the duration of an inspiratory phase, from which the tidal volume is obtained. The control unit 38 derives a desired pressure change by the blower unit 12 from a difference between the measured tidal volume and the preset tidal volume. This leads to a new desired pressure set point of the blower unit 12.

The control unit 38 then derives from this pressure set point a speed set point, preferably by means of a data set, which has a characteristic. Such a characteristic relates pressure values to speeds of the blower unit. The control unit 38 then selects a control signal for the blower unit 12 such that the blower unit 12 assumes or implements the speed set point. This then leads to a volume-controlled ventilation.

It can consequently be stated in summary that the control unit 38 is configured to determine a tidal volume from the flow sensor signal and further to determine a speed set point of the blower unit 12 as a function of the determined tidal volume and the preset tidal volume set point and to change the speed of the blower unit such that a volume-controlled ventilation is carried out.

A controller implemented in hardware or in firmware, which may likewise be comprised by the control unit 38, may, of course, also be considered instead of a control algorithm implemented in software. For example, a proportional algorithm/P controller, a proportional integral algorithm/PI controller or a proportional-integral-differential algorithm/PID controller may be considered as a control algorithm/controller.

Figure 6:
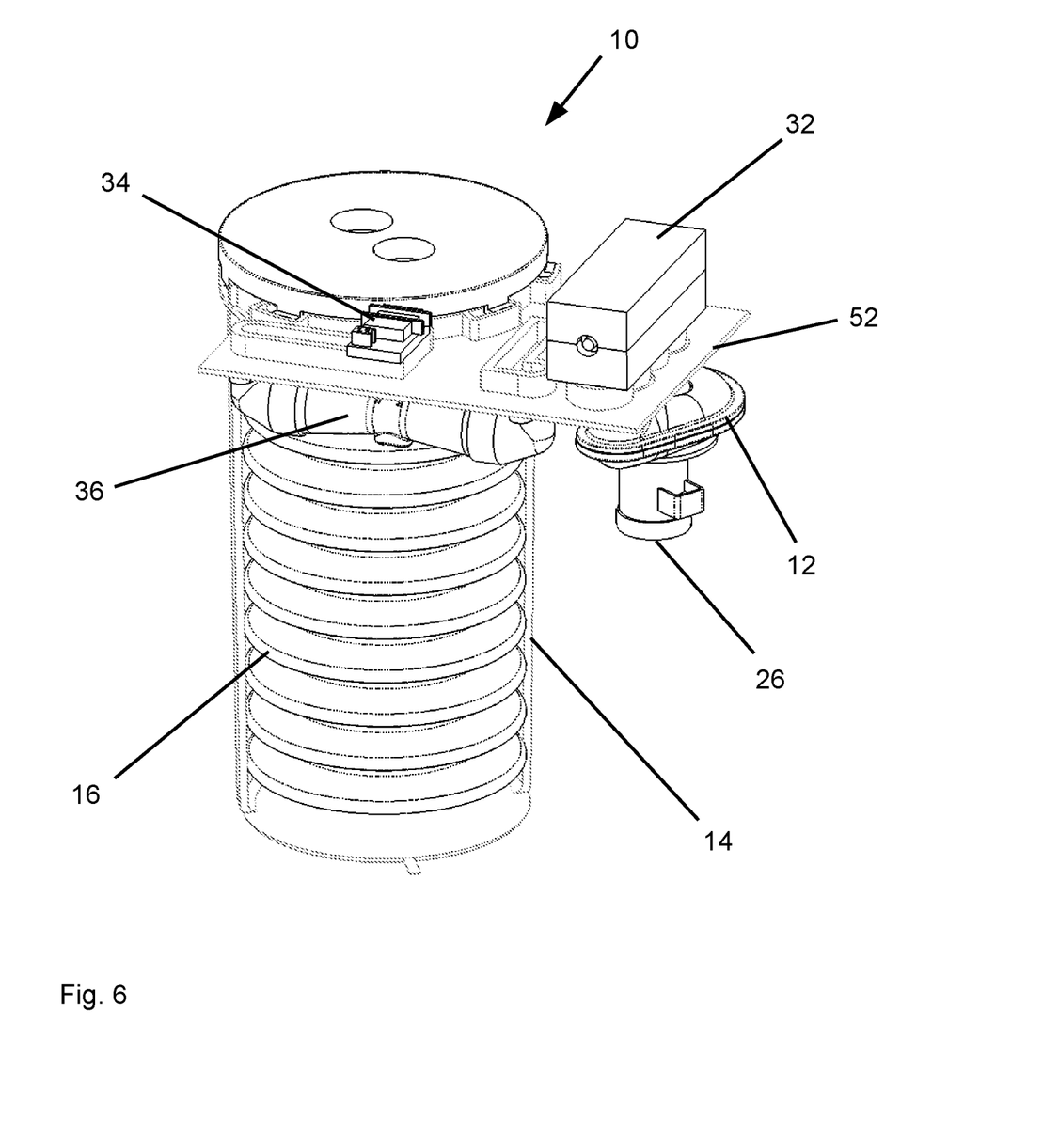
FIG. 6 is an isometric view of an embodiment of a ventilation drive.

The view in FIG. 6 finally shows an isometric view of a ventilation drive 10 according to the solution being proposed here. A housing made of a transparent plastic is used as the pressure chamber 14, so that a movement of the bag 16 configured in the form of a bellows here in the interior of the pressure chamber 14 can readily be observed. The bag 16 may be operated both as an upright bag 16 and as a hanging bag 16. An EPDM (ethylene-propylene-diene rubber) membrane may be considered for use as the material for the bag 16. Such a membrane is characterized by good anesthetic resistance as well as good sterilizability. The internal volume of the bag 16 is coupled at least to the inspiratory branch 20 of a ventilation line in the manner known per se. The blower unit 12 can be coupled on its outlet side to the internal volume of the pressure chamber 14, namely, to the internal volume remaining outside the bag 16 and is coupled to this at least at times during the operation depending on the switching position of the directional control valve 32.

A pressure difference between an actual ventilation patient at the patient and a pressure changed in the ventilation drive 10 by the elasticity of the bag 16 and/or by the weight of the bag 16 is compensated within the framework of the pressure control outlined above, for example, in the form of an adjustment of the support points 50.

Figure 2:
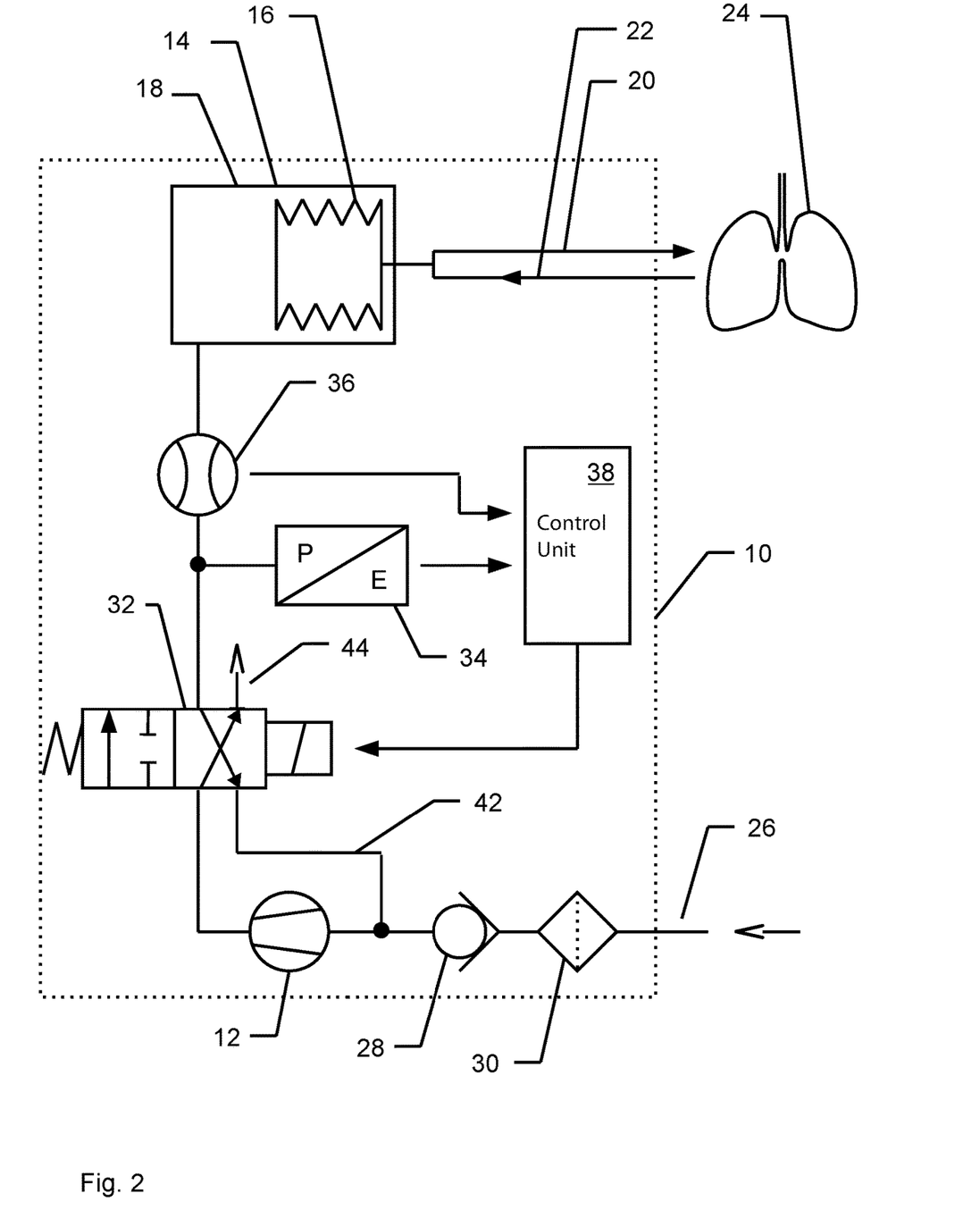
FIG. 2 is a schematic view showing a ventilation drive as is shown in FIG. 1, but with another switching position of a switching element comprised by the ventilation drive.
Figure 3:
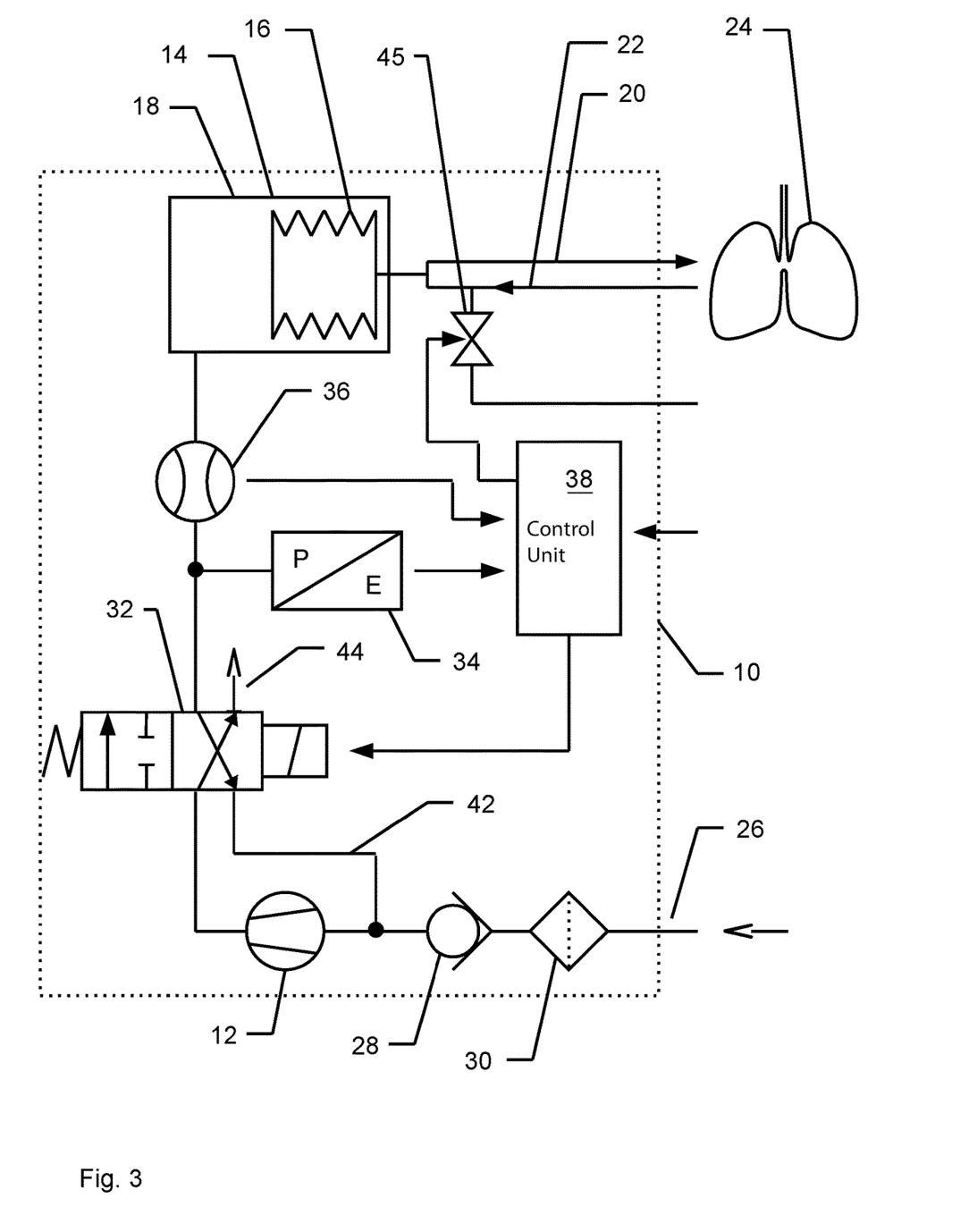
FIG. 3 is a schematic view showing a ventilation drive as is shown in FIG. 1 and FIG. 2, with an actuatable shut-off valve in the breathing circuit adjoining the ventilation drive.

All components of the ventilation drive 10 are arranged in the embodiment shown in FIG. 6 on a support structure, here a plastic assembly unit 52 acting as a support structure here, the support structure optionally also comprising all the gas-carrying ducts, namely, all the gas paths that are shown in FIG. 1 and FIG. 2 and extend indirectly or directly between the pressure chamber 14 and the air inlet 26. A support structure that comprises gas-carrying ducts is configured, for example, in the form as it is described in DE 10 2008 057 180 B (corresponding to U.S. Pat. No. 8,356,596).

The cover plate and the sides of the ducts are not shown in FIG. 6 to illustrate the ducts comprised by the support structure. Reference number 36 designates in FIG. 6 a possible location at which the flow sensor 36 is arranged.

Individual essential aspects of the description presented here can finally be briefly summarized as follows: Proposed are a ventilation drive 10 for an anesthesia device and a method for operating such a ventilation drive 10, wherein this comprises a blower unit 12, a pressure chamber 14 and a flexible bag 16 located in the pressure chamber 14, wherein the internal volume of the bag 16 is coupled to an inspiratory branch 20 of a ventilation line and wherein the blower unit 12 can be coupled to the internal volume of the pressure chamber 14 on an outlet side and to an air inlet 26 for feeding ambient air on an inlet side. It is possible in this way to generate a particular ventilation profile 40 entirely by means of the blower unit 12.

The blower unit is preferably a radial compressor. The radial compressor preferably has a speed range of 0-80,000 rpm and a peak pressure of 100 mbar.

While specific embodiments of the invention have been shown and described in detail to illustrate the application of the principles of the invention, it will be understood that the invention may be embodied otherwise without departing from such principles.

The invention claimed is:

1. A ventilation drive comprising:
    a blower unit;
    a pressure chamber; and
    a flexible bag located in the pressure chamber;
    an air inlet, wherein an internal volume of the bag is coupled to an inspiratory branch of a ventilation line, and the blower unit is configured to be coupled to an internal volume of the pressure chamber on an outlet side of the blower unit and to the air inlet for supplying ambient air on an inlet side of the blower unit;
    a flow sensor between the outlet side of the blower unit and the pressure chamber; and
    a directional control valve between the blower unit and the pressure chamber, wherein a first gas path and a second path are configured to be switched by means of the directional control valve, wherein the blower unit is configured to deliver ambient air drawn in from the surrounding area into the pressure chamber by means of the first gas path and wherein the blower unit is configured to deliver air leaving the pressure chamber into the surrounding area by means of the second gas path.

2. A ventilation drive in accordance with claim 1, further comprising a control unit configured to change the speed of the blower unit as a function of a flow sensor signal of the flow sensor.

3. A ventilation drive in accordance with claim 2, wherein the control unit is configured to change the speed of the blower unit as a function of the flow sensor signal as well as of a preset flow set point.

4. A ventilation drive in accordance with claim 3, wherein the control unit is configured to change the speed of the blower unit as a function of the flow sensor signal as well as of the preset flow set point such that a flow-controlled ventilation is carried out.

5. A ventilation drive in accordance with claim 2, wherein the control unit is configured to change the speed of the blower unit as a function of the flow sensor signal as well as of a preset tidal volume set point.

6. A ventilation drive in accordance with claim 5, wherein the control unit is configured to determine a tidal volume from the flow sensor signal as well as further to change the speed of the blower unit as a function of the determined tidal volume and of the preset tidal volume set point, such that a volume-controlled ventilation is carried out.

7. A ventilation drive in accordance with claim 1, further comprising a pressure sensor and a control unit is configured to change the speed of the blower unit as a function of a pressure sensor signal of the pressure sensor.

8. A ventilation drive in accordance with claim 7, wherein the control unit is configured to change the speed of the blower unit as a function of the pressure sensor signal as well as of a preset pressure set point such that a pressure-controlled ventilation is carried out.

9. A ventilation drive in accordance with claim 1, further comprising a bypass from the directional control valve to an inlet side of the blower unit.

10. A ventilation drive in accordance with claim 9, further comprising a nonreturn valve on the inlet side of the blower unit, wherein the bypass is connected to a connection between the nonreturn valve and the blower unit.

11. A ventilation drive in accordance with claim 1, further comprising a pressure sensor and a control unit for processing at least one measured value originating from the pressure sensor or from the flow sensor and for actuating the directional control valve as a function of the measured value and further as a function of a ventilation profile preset or presettable by the control unit.

12. A method for operating a ventilation drive, the method comprising the steps of:
    providing a ventilation drive comprising a blower unit, a pressure chamber, a flexible bag located in the pressure chamber, an air inlet, wherein an internal volume of the bag is coupled to an inspiratory branch of a ventilation line, the blower unit being configured to be coupled to an internal volume of the pressure chamber on an outlet side of the blower unit and to the air inlet for supplying ambient air on an inlet side of the blower unit and a flow sensor between the outlet side of the blower unit and the pressure chamber;
    providing the ventilation drive with a directional control valve between the blower unit and the pressure chamber, wherein a first gas path and a second path are configured to be switched by means of the directional control valve, wherein the blower unit is configured to deliver ambient air drawn in from the surrounding area into the pressure chamber via the first gas path and wherein the blower unit is configured to deliver air leaving the pressure chamber into the surrounding area via the second gas path;
    drawing ambient air in by means of the blower unit; and
    delivering the drawn ambient air into the pressure chamber for compressing the bag as well as for displacing a part of the breathing gas volume present in the bag into the inspiratory branch.

13. A method in accordance with claim 12, wherein the ventilation drive is switched cyclically over between an inspiratory phase and an expiratory phase and wherein the switchover comprises a switching over of the directional control valve, such that the first gas path is switched by means of the directional control valve for ambient air drawn by means of the blower unit into the pressure chamber during the inspiratory phase and the second gas path is switched for air leaving the pressure chamber during the expiratory phase.

14. A medical device with a ventilation drive, the ventilation drive comprising:
    a blower unit;

a pressure chamber;
a flexible bag located in the pressure chamber;
an air inlet, wherein an internal volume of the bag is coupled to an inspiratory branch of a ventilation line, the blower unit being configured to be coupled to an internal volume of the pressure chamber on an outlet side of the blower unit and to the air inlet for supplying ambient air on an inlet side of the blower unit;
a flow sensor between the outlet side of the blower unit and the pressure chamber; and
a directional control valve between the blower unit and the pressure chamber, wherein a first gas path and a second path are configured to be switched by means of the directional control valve, wherein the blower unit delivers ambient air drawn in from the surrounding area into the pressure chamber via the first gas path and wherein the blower unit delivers air leaving the pressure chamber into the surrounding area via the second gas path.

15. A medical device in accordance with claim 14, further comprising
the ventilation line, which is connected to the bag and which comprises the inspiratory branch and an expiratory branch;
an actuatable shut-off valve in the ventilation line, wherein the ventilation drive is configured to be switched cyclically over between an inspiratory phase and an expiratory phase, wherein the shut-off valve is configured to be actuated for opening for an emergency ventilation during a prolonged expiratory phase and wherein the expiratory branch is configured to be coupled to the ambient air in the opened state.

16. A medical device in accordance with claim 14, further comprising a control unit configured to change the speed of the blower unit as a function of a flow sensor signal of the flow sensor as well as of a preset flow set point.

17. A medical device in accordance with claim 14, further comprising:
a bypass from the directional control valve to an inlet side of the blower unit; and
a nonreturn valve on the inlet side of the blower unit, wherein the bypass is connected to a connection between the nonreturn valve and the blower unit.

18. A medical device in accordance with claim 14, further comprising a pressure sensor and a control unit configured to process at least one measured value originating from the pressure sensor or from the flow sensor and for actuating the directional control valve as a function of the measured value and further as a function of a ventilation profile preset or presettable by the control unit.

* * * * *